United States Patent
Mehl

[11] Patent Number: 5,279,306
[45] Date of Patent: Jan. 18, 1994

[54] BIOPSY NEEDLE

[75] Inventor: Donald N. Mehl, Minnetonka, Minn.

[73] Assignee: Creative Research and Manufacturing, Minnetonka, Minn.

[21] Appl. No.: 734,915

[22] Filed: Jul. 24, 1991

Related U.S. Application Data

[60] Continuation of Ser. No. 484,681, Feb. 23, 1990, abandoned, which is a division of Ser. No. 264,975, Oct. 31, 1988, Pat. No. 4,922,602, which is a continuation of Ser. No. 134,155, Dec. 17, 1987, abandoned, which is a continuation of Ser. No. 605,809, May 1, 1984, abandoned, which is a continuation of Ser. No. 354,421, Mar. 3, 1982, abandoned, which is a continuation-in-part of Ser. No. 244,015, Mar. 16, 1981, abandoned.

[51] Int. Cl.$^5$ .............................................. A61B 10/00
[52] U.S. Cl. ..................................... 128/753; 128/754
[58] Field of Search .......................... 128/751-; 606/197, 198

[56] References Cited

U.S. PATENT DOCUMENTS

| | | |
|---|---|---|
| 2,850,007 | 9/1958 | Lingley . |
| 2,985,209 | 5/1961 | Novelo . |
| 3,175,554 | 3/1965 | Stewart . |
| 3,330,268 | 7/1967 | Goldsmith . |
| 3,470,604 | 10/1969 | Zenick . |
| 3,628,524 | 12/1971 | Jamshidi . |
| 3,995,619 | 12/1976 | Glatzer . |
| 4,163,446 | 8/1979 | Jamshidi . |
| 4,258,722 | 3/1981 | Sessions et al. . |
| 4,262,676 | 4/1981 | Jamshidi . |
| 4,266,555 | 5/1981 | Jamshidi . |
| 4,314,565 | 2/1982 | Lee . |
| 4,356,828 | 11/1982 | Jamshidi . |
| 4,379,458 | 4/1983 | Bauer et al. . |
| 4,469,109 | 9/1984 | Mehl ..................................... 128/753 |

*Primary Examiner*—William E. Kamm
*Assistant Examiner*—Robert L. Nasser, Jr.
*Attorney, Agent, or Firm*—Hugh D. Jaeger

[57] ABSTRACT

Biopsy needle for bone marrow biopsies or the like including a cannula, a cannula housing supporting the cannula, and a stylet including a stylet cap supporting the stylet wherein the stylet engages into the cannula in a predetermined relationship and the stylet cap interlocks to the cannula housing. The cannula housing includes vertical wings extending outwardly from the housing for engagement with the palm of a physician's hand, a cannula having formed ends which engage and secure into the cannula housing, and an elongated button extending outwardly from the top of the cannula housing for detent locking with the stylet cap providing for alignment of the stylet to the cannula of the biopsy needle. The stylet includes a longitudinal member having a ground and buffered beveled end maintaining a knife-sharp edge around the tip, and the other end of the stylet is bent and molded into the stylet cap where the stylet cap includes a spring detent locking groove for interlocking with the button of the cannula housing. The stylet inserts into the cannula and with a twist locks about the top of the cannula with a positive digital sensory feedback signal to the physician.

5 Claims, 2 Drawing Sheets

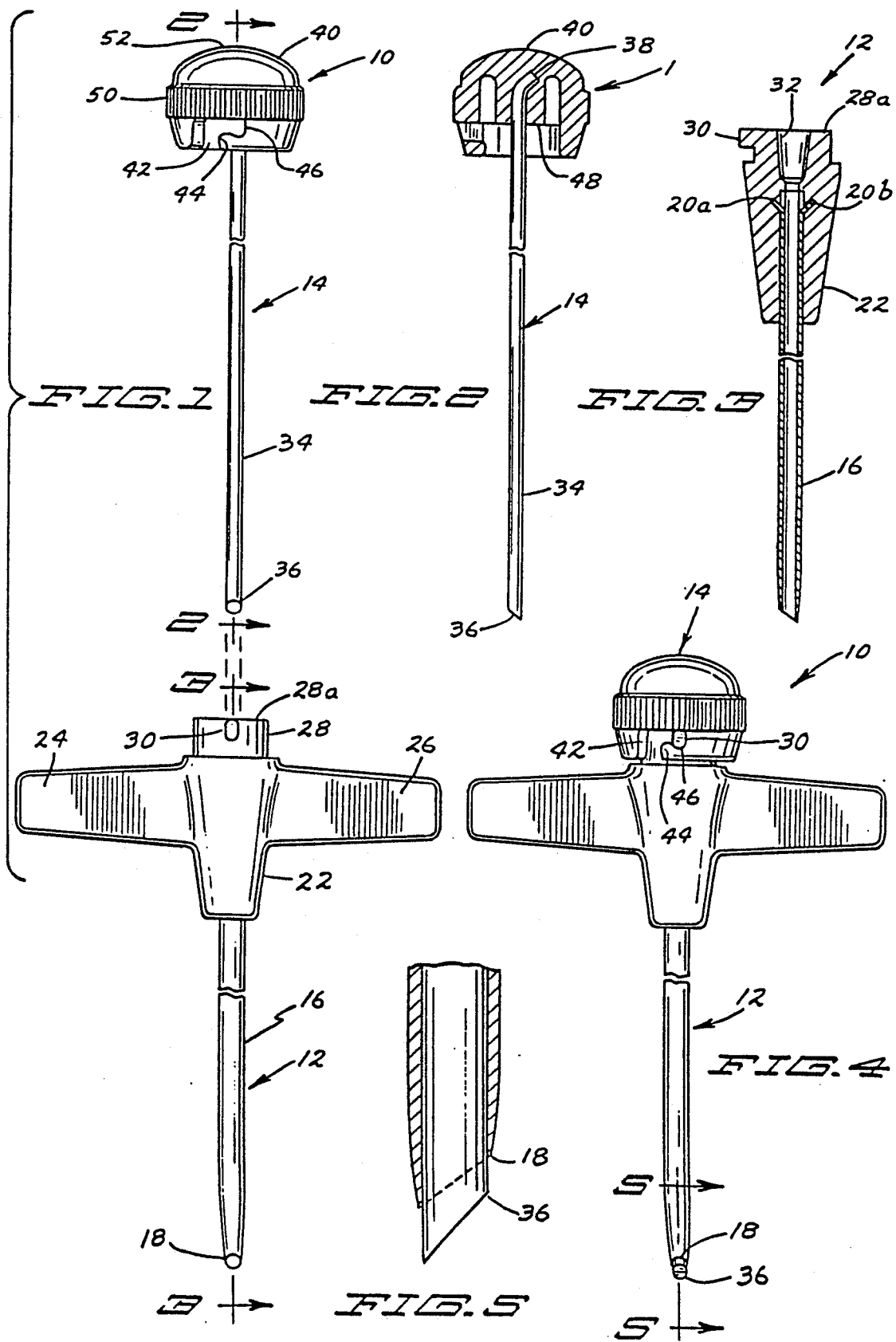

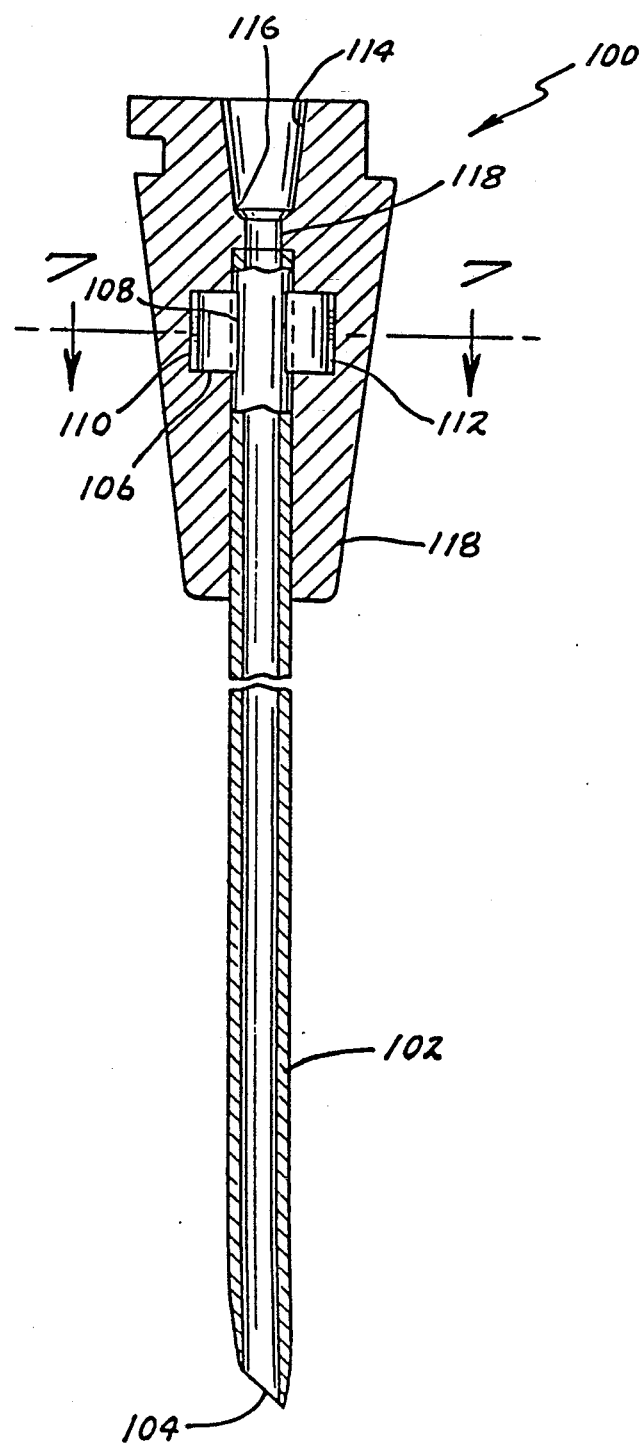

BIOPSY NEEDLE

CROSS REFERENCES TO CO-PENDING APPLICATIONS

This application is a continuation of U.S. Ser. No. 07/484,681, filed Feb. 23, 1990 now abandoned, which is a division of U.S. Ser. No. 07/264,975, filed Oct. 31, 1988, entitled "Biopsy Needle"; which is a Continuation of U.S. Ser. No. 07/134,155, filed Dec. 17, 1987, now abandoned; which is a continuation of U.S Ser. No. 06/605,809, filed May 1, 1984, now abandoned; which is a continuation of U.S. Ser. No. 06/354,421, filed Mar. 3, 1982, now abandoned; which is a Continuation-in-Part of U.S. Ser. No. 06/244,015, filed Mar. 16, 1981, now abandoned, all by Donald N. Mehl and assigned to same assignee.

BACKGROUND OF THE INVENTION

1. Field of the Invention

The present invention pertains to a surgical instrument and, more particularly, pertains to a bone marrow biopsy needle which can be either disposable or reusable. This needle includes a tubular cannula member having a flanged clip which is molded into the housing.

2. Description of the Prior Art

The prior art biopsy needles have all presented some type of drawbacks when used by the physician or surgeon, and which are particularly less than desirable. Some prior art instruments are disposable and cast with very few structural details attended to, with the result that the interlocking between the stylet and the cannula provides for considerable play and the instrument can come apart in the user's hands, resulting in injury not only to the patient but more so to the user by the sharp metal edges poking upwards into the physician's hands. Other prior art devices have some form of interlocking structure but the interlocking structure is not positive, resulting in play between the cannula and stylet during the process of incision into the patient resulting in considerable discomfort. Other types of prior art structures have numerous components which during surgery are not practical in utilization by the user due to the screwing and unscrewing of the fittings.

More importantly, all of the prior art devices have grips which do not really fit into the physician's hand to provide for positive gripping by the physician but have grips which are required to be engaged by the physician in a negative way making the process of biopsy as uncomfortable to the physician/surgeon using the biopsy needle as to the patient. The prior art has failed to recognize that the handles of a biopsy needle must securely engage into the physician's or surgeon's palm for optimum control of the instrument during a biopsy. It is also necessary that the stylet and cannula be engaged to each other during the biopsy process for providing total control to the physician or surgeon.

Prior art needles have secured cannula tubes into the cannula housing in numerous ways providing increased manufacturing processes, resulting in increased end cost to the patient. The prior art has been lacking a needle having a needle readily and cost effectively secured such as through molding into the cannula housing.

The present invention overcomes the disadvantages of the prior art references by providing a biopsy needle having a winged handle and detent locking between the stylet and cannula.

SUMMARY OF THE INVENTION

The general purpose of the present invention is to provide a bone marrow biopsy needle having a cannula and a stylet, both of which engage and interlock with respect to each other, and which can be conveniently grasped by the physician or surgeon in the palm of the hand to provide secure control during the biopsy process.

According to one embodiment of the present invention, there is provided a biopsy needle having a cannula and stylet which interlock with each other, the cannula including a cannula having one end with at least one and preferably two formed members extending outwardly from the end, the other end having a swaged bevel ground and buffed tip providing sharp knife edges in the range of 30-40' with respect to a molded housing, the molding housing molded about the formed members for securing thereto and including two vertically positioned hand wings of decreasing size extending outwardly therefrom, a button extending outwardly from an upward vertical member of reduced diameter with respect to the housing, and an internal bore extending through the housing to the top of the formed end of the cannula for accepting a syringe for drawing of bone marrow during the biopsy, and a stylet including one end having a bend for securing into a stylet cap and the other end having a beveled end in the range of 30-60' and buffed to a polished end having a knife-sharp edge about the tip, the stylet cap secured about the bent end of the stylet and having a spring detent locking groove for engaging under and about the button of the cannula in a detented air-locking fashion, and an interior bore of a height to mate with the vertical member of the cannula and engage on the rim of the cannula formed between the housing and the vertical member whereby the stylet is engaged into the cannula housing and detent locking groove in the stylet cap providing for proper engagement between the knife-sharp edges of the cannula and the stylet, thereby providing for proper instrumentation during biopsy.

According to another embodiment of the present invention, there is provided a needle including a molded cannula housing, a tubular cannular member, cylindrical cannula clip having at least one outwardly extending flange and preferably two outwardly extending flanges extending outwardly from the cylindrical axis of the tube and the clip, opposing each other and forming an angle of 45-135' with respect to each other, and soldered to an upper portion of the tubular cannula member whereby the cannula housing is molded about the tubular cannula member and the cannula clip thereby securing the same in the cannula housing.

A significant aspect and feature of the present invention is a biopsy needle having wing-shaped handles facilitating gripping and engagement by the physician or surgeon user.

Another significant aspect and feature of the present invention is an interlocking stylet and cannula providing for not only interlocking of the structural members in a positive detent fashion but also predetermined orientation between the knife sharp edges of the cannula and the stylet. The interlocking distance from the cannula, providing for consistent and secure biopsy surgery.

An additional significant aspect and feature is a tubular cannular member which is firmly and securely molded in position in the cannular housing through the molded engagement of the cannular clip which is soldered to the tubular cannula member. This protects the surgeon's hand during biopsy as well as the patient.

A further significant aspect and feature of the present invention is a bone marrow biopsy needle which can be constructed either as a disposable instrument or as a reusable instrument depending upon the type of molded material chosen for the cannula and stylet housings.

An additional significant aspect and feature of the present invention is a biopsy needle which can be constructed in different sizes for different sized individuals or for different applications.

Having described one embodiment of the present invention, it is the principal object hereof to provide a bone marrow biopsy needle including a cannula and stylet which interlock with each other. The disclosure also applies to needle structure per se, and is not to be construed as being limited to only biopsy needles, as other applications are inherent within the scope of this disclosure.

BRIEF DESCRIPTION OF THE DRAWINGS

Other objects and many of the attendant advantages of this invention will be readily appreciated as the same becomes better understood by reference to the following detailed description when considered in connection with the accompanying drawings, in which like reference numerals designate like parts throughout the figures thereof and wherein:

FIG. 1 illustrates a perspective view of a cannula and a stylet;

FIG. illustrates a sectional view of the cannula;

FIG. 3 illustrates a sectional view of the stylet;

FIG. 4 illustrates a view of a biopsy needle including the engaged cannula and stylet;

FIG. 5 illustrates an enlarged section of the cannula and stylet knife-sharp edges oriented with respect to each other;

FIG. 6 illustrates a cross sectional view of an alternative embodiment of the cannular member of the present invention, and;

FIG. 7 illustrates a sectional view taken along line 7—7 of FIG. 6.

DESCRIPTION OF THE PREFERRED EMBODIMENTS

FIG. 1 illustrates a perspective view of a biopsy needle 10 having separated components of a cannula member 12 and a stylet member 14. The cannula member 12 includes a longitudinal cannula 16 having a sharp knife edge 18 which has been swaged, beveled, ground and buffed as later described in detail, formed ends 20a and 20b illustrated in FIG. 2 extending outwardly at an angular tubular relationship, a molded housing 22 of ABS material or the like having the shape as illustrated and having molded thereto left-hand wing 24 and right-hand wing 26, a vertical member 28 extending upwardly, an elongated button 30 extending outwardly, and a chamber 32 running vertically downward from the top of member 28 to the top of the cannula 16 as also illustrated in FIG. 2. The stylet member 14 includes a metal stylet 34 having a sharp edge 36 which has been ground, buffed and polished, a bent end 38 for securing into a molded cap 40, a detent locking groove 42 having a spring member 44 including positive locking member 46. A downward extending boss 48 extends downwardly internal to the cap 40 for engagement with a rim 28a of the cannula housing 22. Locking vertical grooves 50 are provided about the cap for engagement by physician or surgeon user, and a rounded top 52 is provided for an individual's hand.

FIG. 2, which illustrates a cross-sectional view of the cannula member 12, shows the particular detail of the formed ends 20a and 20b securing the cannula 16 into the housing 22 about the vertical chamber 32 which decreases from a large diameter to a small diameter in a lure taper, then to a chamfer, and finally to a diameter which is slightly larger than the internal diameter of the cannula 14 so that a syringe can be inserted into the chamber 32 to draw bone marrow up into the cannula. A probe can be utilized to freely push the bone marrow out through the formed end of the cannula and onto a slide, without damaging or distorting the bone marrow. The detent button 30 and the rim 28a provide for engagement of the stylet member 14 in proper predetermined orientation. The particular detail of the tip 18 of the cannula is also illustrated providing that the angle between the vertical plane and the tip is in the range of 30–45' and preferably 35' plus or minus 5'. The angle between the edge of the cannula and the vertical plane is 13½' plus or minus 1'. This tip structure 18 is obtained through swaging, beveling and grinding, and buffing to provide for a consistent tip for ease of surgery during the biopsy in a process later described in detail.

FIG. 3 illustrates a sectional view of the stylet member 14 where all numerals correspond to those elements previously described. The end of the stylet has an angle between horizontal and the edge of 45' plus or minus 2' while the angle may be in the range of 30–60'. The tip is buffed and polished to maintain a sharp knife edge. The upper end 38 of the stylet 34 is bent for securing into the cap 40.

MODE OF OPERATION

FIG. 4 illustrates the biopsy needle 10 of the present invention where the stylet member 14 is engaged and interlocked to the cannula member 12. The detent button 30 provides for locking of the members 12 and 14 together by engagement through the groove 42, and up and over the spring member 44 into the positive locking detent 46. A spring member 44 provides a positive sensory digital feedback signal that the members are engaged where button 30 resides in the chamber area of positive locking member 46. The button 30 and positive locking chamber 46 always provide that the knife edges 18 of the cannula 16 and 36 of the stylet 34 are always oriented with respect to each other as illustrated in the figure, and as also illustrated in FIG. 5, providing least minimum effort on the physician's/surgeon's part during the biopsy surgery. The boss 48 of the stylet member 14 seats the stylet onto the cannula at a proper predetermined distance and provides for the orientation of the knife edges. The beveled tips of the stylet and cannula provide for the proper cutting action through the bone due to the wedge action of the tips. The particular angles of the wedges and orientation with respect to each other is one of the keys to obtaining a suitable bone marrow sample during the biopsy process. The contour of the handles 24 and 26 and the winged configuration provide for positive feel to the physician/surgeon during the biopsy. The formed ends 20a and 20b secure the cannula 16 into the housing 22, and maintain round configuration of the cannula tube end 16 in the housing 22, providing for passage of a sample without damaging or distorting the sample.

The end 18 of the cannula 16 is processed according to the predetermined relationship set forth below where:

offset = ½(tan bevel angle)·tan(tip angle)·(I.D.)) and where I.D. is internal diameter of the cannula 16 and offset to a distance between the grinding centerline and the cannula tube centerline.

In processing the cannula, first the cannula is formed at the housing end and then swaged over a mandrel to a predetermined internal diameter over a predetermined length from the lower end. Then the cannula is eccentrically rotated about the offset centerline and ground at the same time to achieve the 35' plus or minus 5' tip angle in conjunction with 13 ½' plus or minus 1' chamfer beveled angle. The beveling of the edge is done at specific orientation to the housing as illustrated in FIG. 2 of the drawing to obtain the predetermined result. After the rotating and grinding operation, the end is buffed and blended to the sharp knife edge for achieving the product by process as illustrated in FIG. 5.

DESCRIPTION OF ALTERNATIVE EMBODIMENT

FIG. 6 illustrates a sectional view of an alternative embodiment of a cannula 100. A tubular cannula member 102 having a preformed end 104 and includes a cannula clip 106 soldered to an upper portion of the member 102 as now described in detail. The cannula clip 106 includes a partial cylindrical member 108 with two outwardly extending flanges 110 and 112 at an angle with respect to each other. The clip 106 has a finite height and is soldered, welded, or the like towards an upper portion of the tubular cannula member 102 as illustrated in FIG. 6.

The gradual taper 114 and lured taper 116 decreases to a constant diameter 118 substantially equal to the inner diameter of the tubular cannula member 102 and mates thereto forming a smooth junction. The cannula housing 118 having a preferred geometrical shape is molded about the tubular cannula member 102 including the clip 106 with flanges 110 and 112 further securing member 102 in engagement to and within the housing 118. The clip 106 soldered or the like to the tube 102 provides for positive and secure engagement to the housing 118. All other structure for engaging to the stylet is identical as previously described for FIGS. 1-5.

FIG. 7 illustrates a sectional view taken along a line 7—7 of FIG. 6 where all numerals correspond to those elements previously described. Attention is drawn to the angle of the flanges 110 and 112 while the cylindrical member 108 is illustrated partially encompassing the tubular cannula member 102. The angle of 110-112 is in the range of 45-135'.

Operation of the cannula 100 of FIGS. 6 and 7 is identical to that of FIGS. 1-5 as previously described.

Various modifications to the biopsy needle of the present invention can be made without departing from the apparent scope thereof. The disclosure is applicable to generic needles and is not to be construed as being limited to biopsy needles. The disclosure is applicable to attachment on a needle to structure in general and for forming a predetermined tip at the end of the needle.

Having thus described the invention, what is claimed is:

1. A biopsy needle comprising:
   a. a cannula having a proximal end and a distal end with a lumen transversing said cannula from said proximal end to said distal end;
   b. a solid stylet having a proximal end and a distal end removably inserted within said lumen of said cannula;
   c. a housing coupled to said proximal end of said cannula;
   d. a cap fixedly attached to said proximal end of said solid stylet having a bore sufficiently large to accept said housing; and,
   e. means attached to said housing and said cap for sealingly coupling said housing to said cap by rotating said cap a fraction of a turn in a first direction, and for releasing said housing from said cap by rotating said cap a fraction of a turn in a second direction, said means providing a positive sensory digital feedback signal indicating coupling of said housing to said cap upon rotating said cap in said first direction.

2. A biopsy needle according to claim 1 wherein said distal end of said cannula is cut diagonal to the longitudinal axis of said cannula.

3. A biopsy needle according to claim 2 wherein said distal end of said stylet is cut diagonal to the longitudinal axis of said stylet.

4. A biopsy needle according to claim 3 wherein said diagonal cut of said stylet is aligned with said diagonal cut of said cannula when said housing is sealingly coupled to said cap.

5. The biopsy needle of claim 1 wherein said distal ends of said cannula and of said stylet terminate in knife edge, and wherein said means attached to said housing and said cap comprises a button extending outwardly from said housing and a detent locking groove and spring member in said cap to engage and lock said button in said cap and thereby orient said knife with respect to each other at the same predetermined position.

* * * * *

REEXAMINATION CERTIFICATE (3526th)

United States Patent [19]

Mehl

[11] B1 5,279,306

[45] Certificate Issued    *Jun. 2, 1998

[54] BIOPSY NEEDLE

[75] Inventor: Donald N. Mehl, Minnetonka, Minn.

[73] Assignee: Creative Research and Manufacturing of Minnesota, Minnetonka, Minn.

[*] Notice: The term of this patent shall not extend beyond the expiration date of Pat. No. 4,469,109.

Reexamination Request:
No. 90/004,220, Apr. 10, 1996

Reexamination Certificate for:
Patent No.: 5,279,306
Issued: Jan. 18, 1994
Appl. No.: 734,915
Filed: Jul. 24, 1991

[*] Notice: The portion of the term of this patent subsequent to Sep. 4, 2001, has been disclaimed.

Related U.S. Application Data

[60] Continuation of Ser. No. 484,681, Feb. 23, 1990, abandoned, which is a division of Ser. No. 264,975, Oct. 31, 1988, Pat. No. 4,922,602, which is a continuation of Ser. No. 134,155, Dec. 17, 1987, abandoned, which is a continuation of Ser. No. 605,809, May 1, 1984, abandoned, which is a continuation of Ser. No. 354,421, Mar. 3, 1982, abandoned, which is a continuation-in-part of Ser. No. 244,015, Mar. 16, 1981, abandoned.

[51] Int. Cl.$^6$ ................................................ A61B 10/00
[52] U.S. Cl. ............................................ 128/753; 128/754
[58] Field of Search .................... 128/751–4; 606/197, 606/198

[56] References Cited

U.S. PATENT DOCUMENTS

| | | | |
|---|---|---|---|
| 2,828,744 | 4/1958 | Hirsch et al. | 604/272 |
| 3,628,524 | 12/1971 | Jamshidi | 128/753 |
| 3,860,006 | 1/1975 | Patel . | |
| 4,013,080 | 3/1977 | Froning . | |
| 4,256,119 | 3/1981 | Gauthier . | |
| 4,469,109 | 9/1984 | Mehl | 128/753 |

*Primary Examiner*—Robert L. Nasser, Jr.

[57] ABSTRACT

Biopsy needle for bone marrow biopsies or the like including a cannula, a cannula housing supporting the cannula, and a stylet including a stylet cap supporting the stylet wherein the stylet engages into the cannula in a predetermined relationship and the stylet cap interlocks to the cannula housing. The cannula housing includes vertical wings extending outwardly from the housing for engagement with the palm of a physician's hand, a cannula having formed ends which engage and secure into the cannula housing, and an elongated button extending outwardly from the top of the cannula housing for detent locking with the stylet cap providing for alignment of the stylet to the cannula of the biopsy needle. The stylet includes a longitudinal member having a ground and buffered beveled end maintaining a knife-sharp edge around the tip, and the other end of the stylet is bent and molded into the stylet cap where the stylet cap includes a spring detent locking groove for interlocking with the button of the cannula housing. The stylet inserts into the cannula and with a twist locks about the top of the cannula with a positive digital sensory feedback signal to the physician.

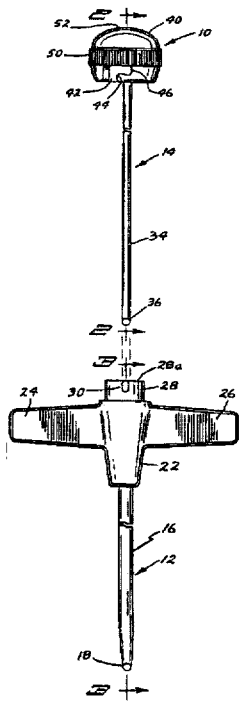

REEXAMINATION CERTIFICATE ISSUED UNDER 35 U.S.C. 307

THE PATENT IS HEREBY AMENDED AS INDICATED BELOW.

Matter enclosed in heavy brackets [ ] appeared in the patent, but has been deleted and is no longer a part of the patent; matter printed in italics indicates additions made to the patent.

AS A RESULT OF REEXAMINATION, IT HAS BEEN DETERMINED THAT:

Claims 2 and 3 are cancelled.

Claims 1, 4 and 5 are determined to be patentable as amended.

1. A bone marrow biopsy needle comprising:
   a. a cannula [adapted for bone marrow biopsy] *rigid along its entire length* having a proximal end and a distal end with a lumen transversing said cannula from said proximal end to said distal end, said distal end of said canula having a cut diagonal to the longitudinal axis of said cannula such that said cannula terminates in a knife sharp edge;
   b. a solid stylet [adapted for bone marrow biopsy] having a proximal end and a distal end removably inserted within said lumen of said cannula said distal end of said stylet having a cut diagonal to the longitudinal axis of said stylet such that said stylet terminates in a knife sharp edge;
   c. a housing coupled to said proximal end of said cannula;
   d. a cap fixedly attached to said proximal end of said solid stylet having a bore sufficiently large to accept said housing; and
   e. means attached to said housing and said cap for sealingly coupling said housing to said cap and for maintaining said distal end of said stylet in a predetermined orientation with respect to said distal end of said cannula such that the knife sharp edge of said cannula and the knife sharp edge of said stylet are substantially parallel during a bone marrow biopsy procedure by rotating said cap a fraction of a turn in a first direction, and for releasing said housing from said cap by rotating said cap a fraction of a turn in a second direction, said means providing a positive sensory digital feedback signal indicating coupling of said housing to said cap upon rotating said cap in said first direction.

4. A biopsy needle according to claim [4] *1* wherein said diagonal cut of said stylet is aligned with the said diagonal cut of said cannula when said housing is sealingly coupled to said cap.

5. The biopsy needle of claim 1 wherein [said distal ends of said cannula and of said stylet terminate in knife edge, and wherein] said means attached to said housing and said cap comprises a button extending outwardly from said housing and detente locking groove and spring member in said cap to engage and lock said button in said cap and thereby orient said knife edges with respect to each other at the same predetermined position.

\* \* \* \* \*